(12) United States Patent
Lucassen et al.

(10) Patent No.: US 8,406,835 B2
(45) Date of Patent: Mar. 26, 2013

(54) PROBE HEAD FOR SPECTROSCOPIC ANALYSIS OF A FLUID

(75) Inventors: Gerhardus Wilhelmus Lucassen, Eindhoven (NL); Wouter Harry Jacinth Rensen, Eindhoven (NL); Michael Cornelis Van Beek, Eindhoven (NL); Marjolein Van Der Voort, Vladenswaard (NL); Bernardus Leonardus Gerardus Bakker, Nijmegen (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1681 days.

(21) Appl. No.: 11/568,363

(22) PCT Filed: Feb. 14, 2005

(86) PCT No.: PCT/IB2005/050564
§ 371 (c)(1),
(2), (4) Date: Oct. 26, 2006

(87) PCT Pub. No.: WO2005/104932
PCT Pub. Date: Nov. 10, 2005

(65) Prior Publication Data
US 2007/0213609 A1  Sep. 13, 2007

(30) Foreign Application Priority Data

Apr. 30, 2004 (EP) .................................. 04101867

(51) Int. Cl.
*A61B 5/1455* (2006.01)
*A61B 5/00* (2006.01)
*G02B 6/44* (2006.01)

(52) U.S. Cl. ........ 600/310; 600/322; 600/473; 600/476; 385/101

(58) Field of Classification Search .................. 600/310, 600/322, 323, 326, 316, 324, 327, 407, 473, 600/476; 385/101
See application file for complete search history.

(56) References Cited

U.S. PATENT DOCUMENTS

| 4,951,049 | A |   | 8/1990  | Whitfield |
|-----------|---|---|---------|-----------|
| 5,598,842 | A | * | 2/1997  | Ishihara et al. ............... 600/322 |
| 5,769,076 | A | * | 6/1998  | Maekawa et al. ............. 600/322 |
| 5,795,295 | A | * | 8/1998  | Hellmuth et al. ............. 600/407 |
| 5,825,488 | A | * | 10/1998 | Kohl et al. ..................... 600/310 |
| 6,465,968 | B1| * | 10/2002 | Sendai ........................ 315/169.3 |
| 6,882,785 | B2| * | 4/2005  | Eichelberger et al. ........ 385/101 |
| 7,133,710 | B2| * | 11/2006 | Acosta et al. ................. 600/316 |
| 2002/0049386 | A1| * | 4/2002 | Yang et al. .................... 600/476 |

(Continued)

FOREIGN PATENT DOCUMENTS

| EP | 0027321 A1 | 4/1981 |
| EP | 1097670 A2 | 5/2001 |

(Continued)

*Primary Examiner* — Eric Winakur
*Assistant Examiner* — Chu Chuan (JJ) Liu

(57) ABSTRACT

A spectroscopic system for determining a property of a fluid flowing through a volume of interest underneath the surface of the skin of a patient is described. The spectroscopic system comprises: a probe head having an objective for directing an excitation beam into the volume of interest and for collecting return radiation from the volume of interest; a base station having a spectroscopic analysis unit and a power supply; and a cable connecting the probe head and the base station for transmission of the return radiation from the probe head to the base station and for providing the probe head with power from the power supply of the base station.

12 Claims, 8 Drawing Sheets

U.S. PATENT DOCUMENTS

Figure 1:
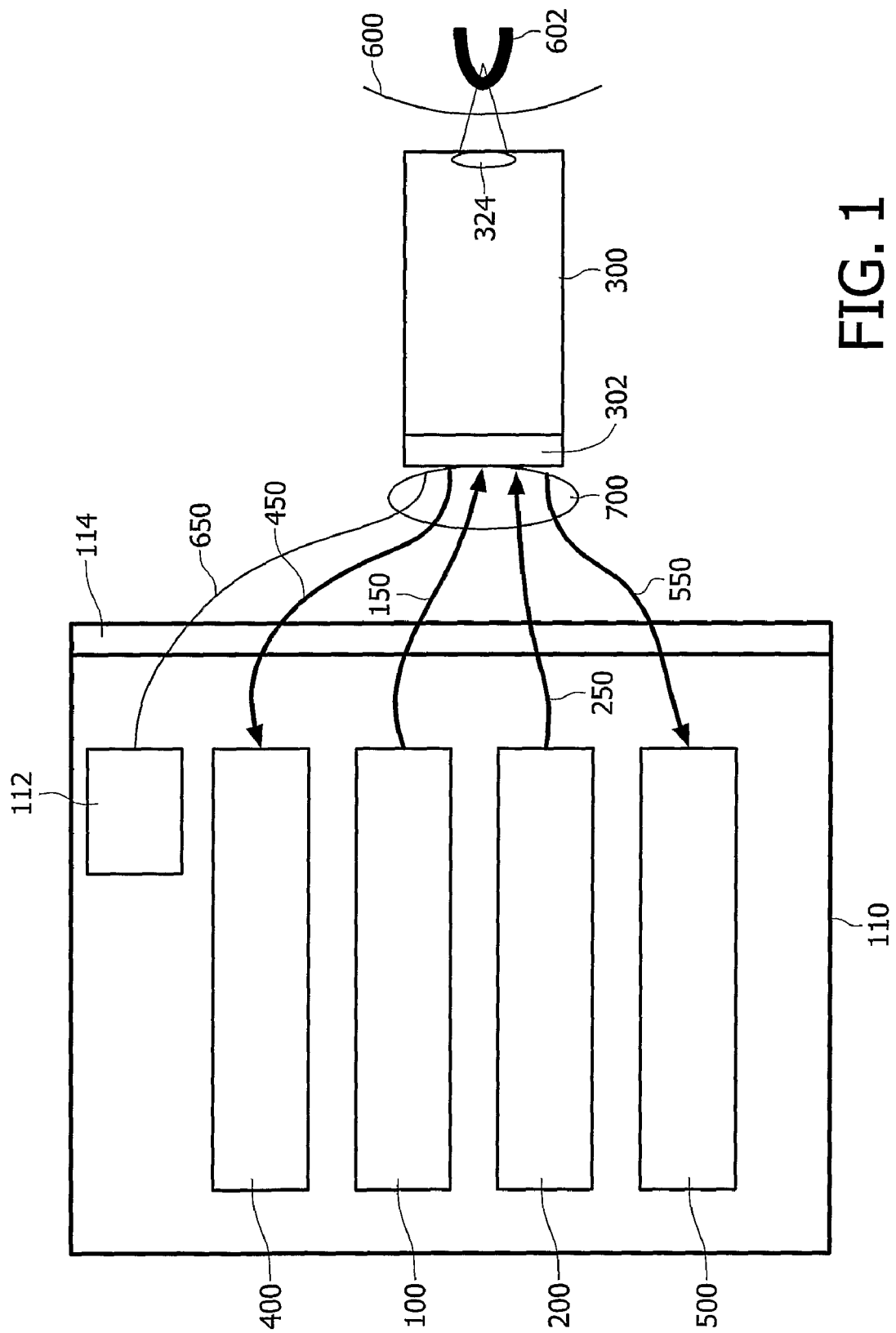

| | | | |
|---|---|---|---|
| 2002/0133065 A1* | 9/2002 | Lucassen et al. | 600/322 |
| 2002/0156380 A1 | 10/2002 | Feld et al. | |
| 2003/0109774 A1* | 6/2003 | Lucassen et al. | 600/322 |

FOREIGN PATENT DOCUMENTS

| | | | |
|---|---|---|---|
| JP | 2003310578 A | 11/2003 | |
| WO | 9322649 | 11/1993 | |
| WO | 0228273 A2 | 4/2002 | |
| WO | 02057758 A1 | 7/2002 | |
| WO | 02057759 A1 | 7/2002 | |
| WO | 03011126 A1 | 2/2003 | |
| WO | 03014920 A2 | 2/2003 | |
| WO | WO/03/076883 * | 9/2003 | 600/316 |
| WO | 2004082474 A1 | 9/2004 | |

* cited by examiner

PROBE HEAD FOR SPECTROSCOPIC ANALYSIS OF A FLUID

The present invention relates to the field of spectroscopic analysis of a fluid and in particular to in vivo non-invasive blood analysis Usage of optical spectroscopic techniques for analytical purposes is as such known from the prior art. WO 02/057758 A1 and WO 02/057759 A1 show spectroscopic analysis apparatuses for in vivo non-invasive spectroscopic analysis of the composition of blood flowing through a blood vessel of a patient. The position of the capillary vessel is determined by a monitoring system in order to identify a region of interest to which an excitation beam for the spectroscopic analysis has to be directed. Preferably, the imaging and the spectral analysis of the region of interest is performed simultaneously. Making use of simultaneous monitoring and spectral analyzing allows to increase the signal to noise ratio or the signal to background ratio of a detectable spectroscopic signal, by optimizing signal from blood. In principle, any monitoring method providing a sufficient visualization of a capillary vessel can be applied.

Making use of the monitoring technique for example allows to visualize, the position of a capillary vessel being relevant for spectroscopic analysis. In this way, the spectroscopic excitation beam can be sufficiently focused and directed into the relevant capillary vessel. By spectrally analyzing the return radiation emerging from the capillary vessel due to a plurality of various scattering processes, the composition of the fluid inside the capillary vessel can be determined.

Since in the prior art, spectroscopic analysis systems for simultaneous monitoring and spectroscopic analysis of a region of interest are fairly large in size and rather inflexible, only designated portions of a body of a patient can be subject to spectroscopic analysis, such as forearm, wrist or fingers of the hand.

However, for many applications a universal spectroscopic analysis of blood vessels within arbitrary body regions would be very advantageous. Body parts that do not allow an easy access for spectroscopic analysis are for example the mouth, inner cheek, nostrils, ear lobes, or other sensitive dermal tissue like in the surrounding of the eyes. In principle spectroscopic analysis systems providing simultaneous spectral analysis and visual monitoring of a region of interest are not designed for examination of those body parts because of their relatively large geometry and rather inflexible optical means for excitation of the region of interest, capturing of scattered radiation and monitoring the region of interest.

The present invention therefore aims to provide a flexible spectroscopic system for determining a property of a fluid flowing through a volume of interest underneath the surface of the skin of a patient.

The invention provides a spectroscopic system for determining a property of a fluid flowing through a volume of interest underneath the surface of the skin of a patient. The inventive spectroscopic system comprises a probe head having an objective for directing an excitation beam into the volume of interest and for collecting return radiation from the volume of interest. Preferably, the objective is adapted for confocally directing the excitation beam into the volume of interest. The inventive spectroscopic system also comprises a base station having a spectroscopic analysis unit and a power supply and further comprises a cable connecting the probe head and the base station for transmission of the return radiation from the probe head to the base station and for providing the probe head with power from the power supply of the base station.

By separating the optical means and the spectroscopic analysis unit of the spectroscopic system and by implementing the rather spacious spectroscopic analysis unit inside the base station allows for a compact design of the probe head. Moreover, by connecting the probe head and the base station via a flexible cable for transmission of the collected return radiation provides a flexible handling of the probe head in order to access arbitrary regions of a body that are difficult to examine. In this way, the invention provides a handheld compact and flexible probe head for non-invasive spectroscopic analysis of biological structures underneath the surface of the skin.

According to a further preferred embodiment of the invention, the spectroscopic system further comprising monitoring means for directing a monitoring beam to the volume of interest and for collecting a monitoring return radiation from the volume of interest.

Preferably, monitoring refers to visual imaging of the volume of interest in order to identify biological structures in the volume of interest and for precisely directing the focal position of the excitation beam into the biological structure. Moreover, monitoring may also refer to a non-visual inspection of the volume of interest. In this case, a biological structure is identified by means of a computer supported analysis system making use of a recognition software that allows to trace a designated biological structure within the volume of interest.

Furthermore, monitoring of the region of interest and the spectroscopic analysis of the region of interest are performed simultaneously. This means that the period of time necessary for monitoring and the period of time necessary for spectroscopic analysis at least partially overlap. The required optical means for directing the monitoring beam to the volume of interest and for collecting the monitoring return radiation from the volume of interest are implemented into the probe head. The monitoring beam source as well as analysis means for transforming the monitoring return radiation into a visual image are provided by the base station but can alternatively also be implemented into the probe head.

Suitable monitoring or imaging methods, include Orthogonal Polarized Spectral Imaging (OPSI), Confocal Video Microscopy (CVM), Optical Coherence Tomography (OCT), Confocal Laser Scanning Microscopy (CLSM), photo-acoustic imaging, ultrasonography and Doppler Based Imaging. Corresponding imaging techniques are disclosed U.S.60/262, 582, EP02732161.1, EP03100689.3, EP03102481.3, the entirety of which is herein incorporated by reference.

According to a further preferred embodiment of the invention, the probe head further comprises a beam combination unit for axially combining the excitation beam and the monitoring beam. By axially combining the excitation beam and the monitoring beam inside the probe head allows to make use of a single objective of the probe head for directing both the excitation beam and the monitoring beam into the volume of interest and for collecting both return radiation and monitoring return radiation from the volume of interest.

According to a further preferred embodiment of the invention, the probe head further comprises a filter unit for spatially separating the return radiation and the monitoring return radiation. The filter unit makes efficient use of e.g. a dichroic mirror featuring a high reflectivity for the wavelength of the return radiation and in contrast featuring a low reflectivity, hence a high transmission for the wavelength of the monitoring return radiation. In this way the spectroscopic optical signal and the monitoring optical signal can effectively be separated allowing for a separate analysis of a visual image and a spectroscopic signal of the volume of interest.

According to a further preferred embodiment of the invention, the probe head further comprises a focusing unit being adapted to move the focal volume of the excitation beam into the volume of interest. Making use of a focusing unit allows to shift the focal position in either transversal or longitudinal direction for precisely directing the focal position of the excitation beam into a particular volume of interest that is visualized by means of the monitoring beam. Since the focal spot size of the excitation beam can be as small as a few µm² it has to be ensured, that the focus of the excitation beam substantially overlaps with the volume of interest or with a designated biological structure within the volume of interest that is subject to spectroscopic analysis. It is therefore advantageous to provide the probe head of the spectroscopic system with a focusing unit allowing for an arbitrary shifting of the focal position of the excitation beam. In this way, the probe head can be rigidly attached to a specific part of the body of the patient while the focal position of the excitation beam can still be spatially shifted.

According to a further preferred embodiment of the invention, the probe head further comprises an optical imaging unit for analyzing the monitoring return radiation. In this embodiment, the monitoring return radiation is directly analyzed by an optical imaging unit providing a visual image of the volume of interest. Hence the visual image is directly analyzed and processed in the probe head. Consequently the monitoring return radiation does not have to be transmitted to the base station. Furthermore, it is also conceivable that even the monitoring beam source is directly implemented into the probe head. Thus only the excitation beam and the return radiation have to be transmitted between the probe head and the base station of the spectroscopic system.

According to a further preferred embodiment of the invention, the base station further comprises a beam combination unit for axially combining the excitation beam and the monitoring beam. In this embodiment both the monitoring beam source and the excitation beam source are located in the base station and being transmitted to the probe head by a single multimode optical fiber provided by the cable connecting the base station and the probe head.

According to a further preferred embodiment of the invention, the base station further comprises a filter unit for spatially separating the return radiation and the monitoring return radiation. The separation of the return radiation and the monitoring return radiation in the base station makes preferable use of a dichroic mirror element featuring different transmission and reflectivity coefficients for elastically and inelastically scattered return radiation.

When the base station of the spectroscopic system comprises both a beam combination unit as well as a filter unit for the excitation and the monitoring beam, the transmission means of the cable connecting the probe head and the base station can be limited to a single multimode optical fiber providing the transmission of the excitation and the monitoring beam and the returning radiation and monitoring return radiation, respectively. Consequently, the probe head neither requires a beam combination unit nor a filter unit for spatially separating the return radiation and the monitoring return radiation. This allows for an extreme compact design of the probe head only featuring an objective for directing the excitation beam and the monitoring beam into the volume of interest and for collecting corresponding return radiation.

According to a further preferred embodiment of the invention, the base station further comprises a focusing unit being adapted to move the focal volume of the excitation beam into the volume of interest. In this way even the shifting means for arbitrarily shifting the focal position of the excitation beam can be implemented into the base station. Thus allowing for an even more compact design of the probe head.

According to a further preferred embodiment of the invention, the base station further comprises an optical imaging unit for analyzing the monitoring return radiation. Hence the monitoring return radiation is processed by the base station in order to obtain a visual image of the volume of interest. In response of the visualization, a particular volume of interest can be selected for precisely directing the focal position of the excitation beam into this particular volume of interest.

According to a further preferred embodiment of the invention, the optical imaging unit is adapted to select the volume of interest and is further adapted to control the focusing unit moving the focal volume of the excitation beam into the volume of interest. In this way, the optical imaging unit can for example autonomously detect a particular biological structure inside the volume of interest being visualized by means of the monitoring return radiation. Autonomous detection or recognition of the biological structures typically makes use of e.g. pattern recognition means that are applicable to the visualized image. Once a biological structure has been recognized within the visualized region of interest, the optical imaging unit is adapted to control the focusing unit in order to shift the focal volume of the excitation beam in such a way, that it substantially overlaps with the position of the recognized biological structure.

In another aspect, the invention provides a probe head for a spectroscopic system for determining a property of a fluid flowing in a volume of interest underneath the surface of the skin of a patient. The spectroscopic system has a base station with a spectroscopic analysis unit and a power supply and may further be implemented according to any one of the above described embodiments. The probe head comprises an objective for directing an excitation beam into the volume of interest and for collecting return radiation from the volume of interest. The probe head is further adapted to be connected to a cable being coupled to the base station. This cable is further adapted to provide transmission of the return radiation from the probe head to the base station and to provide the probe head with power from the power supply of the base station.

In still another aspect, the invention provides a base station for a spectroscopic system for determining a property of a fluid flowing through a biological structure in a volume of interest underneath the surface of the skin of a patient. The spectroscopic system may be implemented according to any one of the above described embodiments. The spectroscopic system has at least a probe head having an objective for directing an excitation beam to the volume of interest and for collecting return radiation from the volume of interest. The inventive base station comprises a spectroscopic analysis unit and a power supply. The inventive base station is adapted to be connected to a cable being coupled to the probe head. The cable is further adapted to provide transmission of the return radiation from the probe head to the base station and to provide the probe head with power from the power supply of the base station.

In still another aspect, the invention provides a cable for connecting a probe head and a base station of a spectroscopic system for determining a property of a fluid flowing through a biological structure in a volume of interest underneath the surface of the skin of a patient. Here, the spectroscopic system may also be implemented according to any one of the above described embodiments. The probe head has an objective for directing an excitation beam into the volume of interest and for collecting return radiation from the volume of interest. The base station has a spectroscopic analysis unit and a power supply and the inventive cable connecting the probe head and the base station comprises at least one optical fiber being adapted to transmit the return radiation from the probe head to the base station and an electrical conducting element being adapted to provide the probe head with power from the power supply of the base station.

According to a further preferred embodiment of the invention, the at least one optical fiber of the inventive cable is further adapted to transmit a monitoring return radiation from the probe head to the base station.

According to a further preferred embodiment of the invention, the at least one optical fiber of the inventive cable is further adapted to transmit a monitoring beam from the base station to the probe head. Preferably, the inventive cable provides bidirectional transmission of both the excitation beam and the monitoring beam and the corresponding return radiation and monitoring return radiation. This allows a rather compact design of the probe head only requiring an objective for focusing the excitation and monitoring beam into a volume of interest and for collecting corresponding return radiation and monitoring return radiation respectively.

It is to be noted, that the present invention is not restricted to a particular type of spectroscopic techniques, as e.g. Raman spectroscopy, but that other optical spectroscopic techniques can also be used. This includes (i) other methods based on Raman scattering including non-linear Raman spectroscopy, such as stimulated Raman spectroscopy and coherent anti-Stokes Raman spectroscopy (CARS), (ii) infra-red spectroscopy, in particular infra-red absorption spectroscopy, Fourier transform infra-red (FTIR) spectroscopy and near infra-red (NIR) diffusive reflection spectroscopy, (iii) other scattering spectroscopy techniques, in particular fluorescence spectroscopy, multi-photon fluorescence spectroscopy and reflectance spectroscopy, and (iv) other spectroscopic techniques such as photo-acoustic spectroscopy, polarimetry and pump-probe spectroscopy. Preferred spectroscopic techniques for application to the present invention are Raman spectroscopy and fluorescence spectroscopy.

Figure 2:
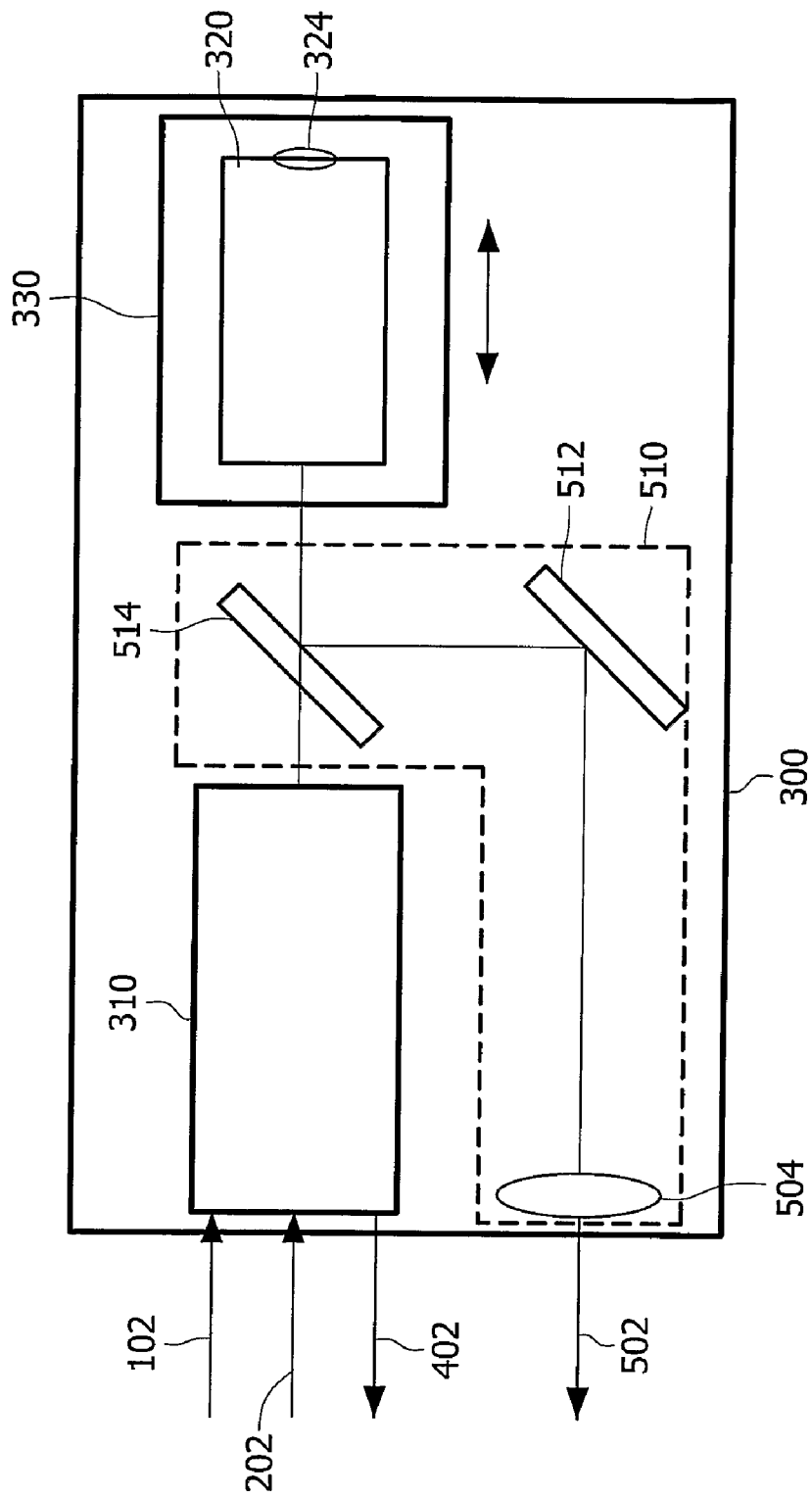
Figure 3:
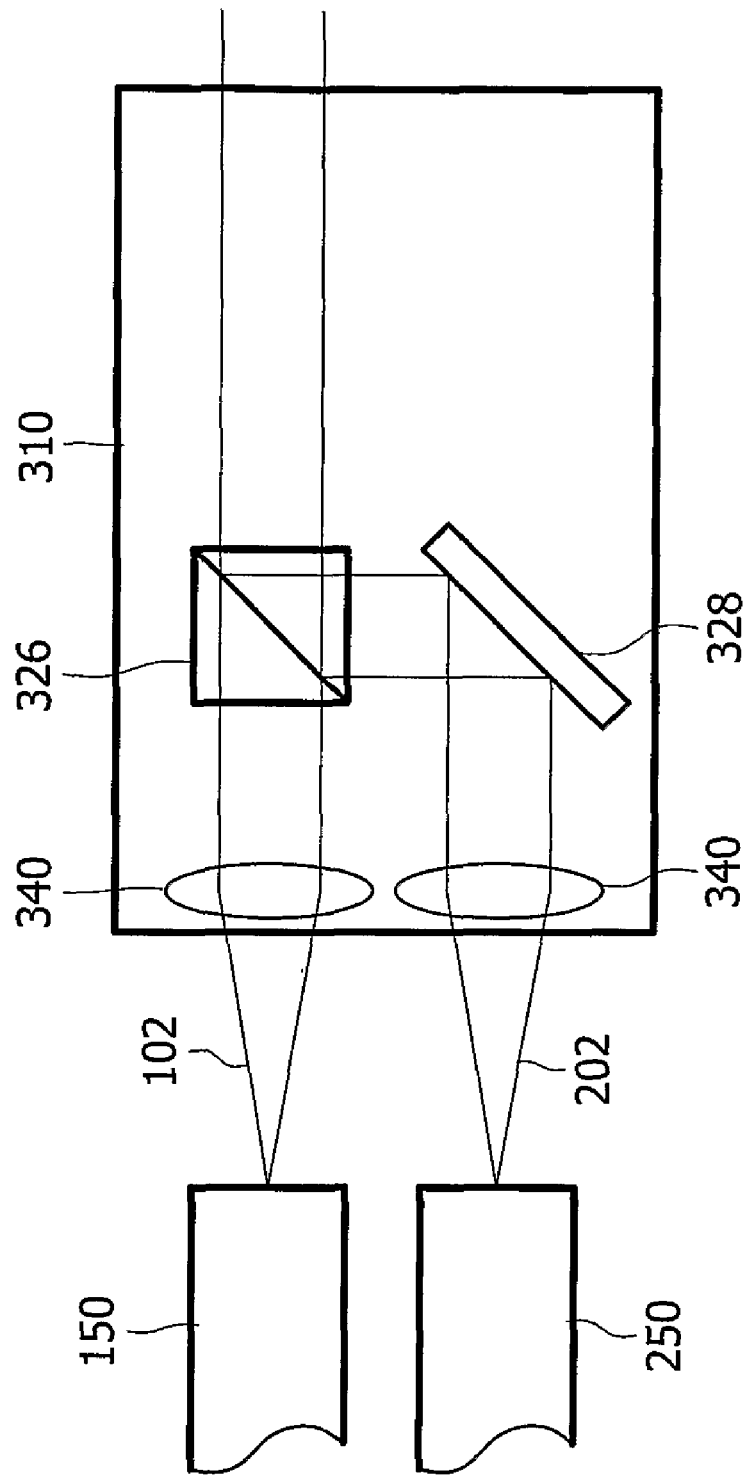
Figure 4:
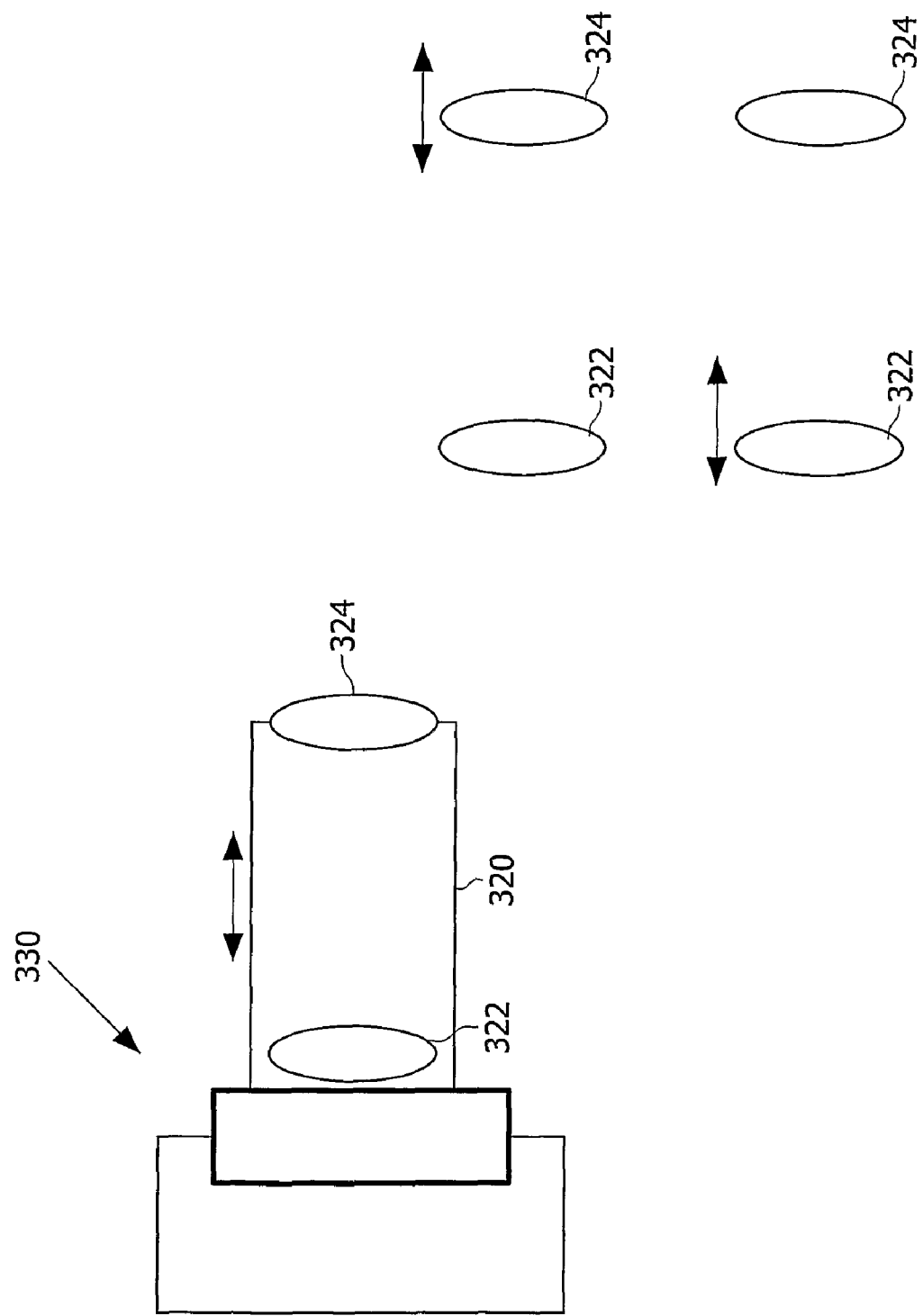
Figure 5:
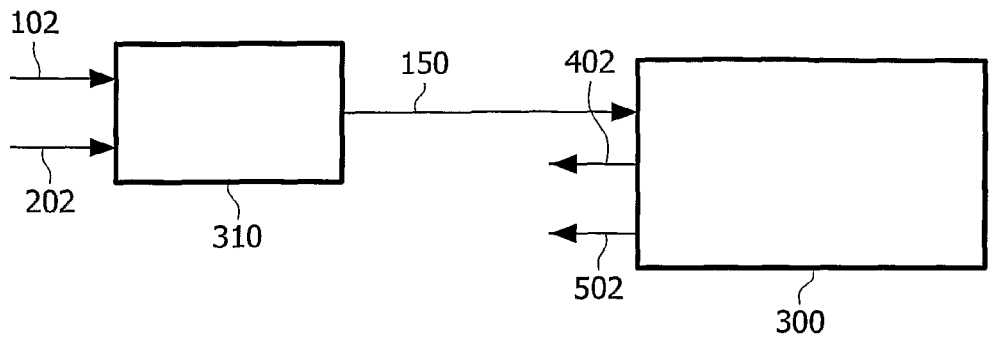
Figure 6:
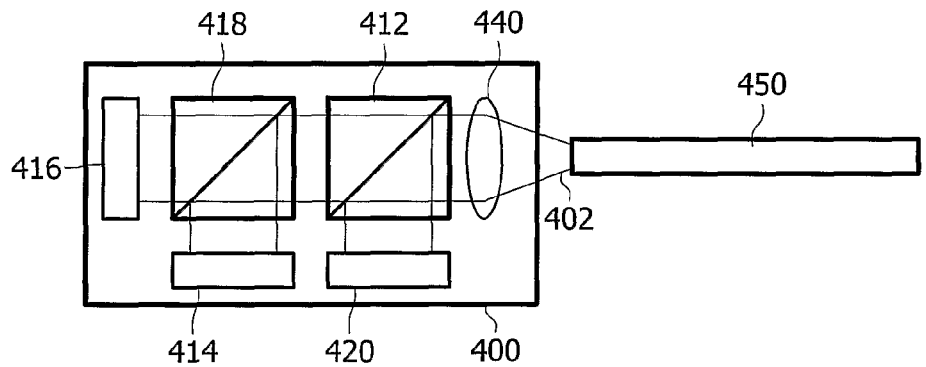
Figure 7:
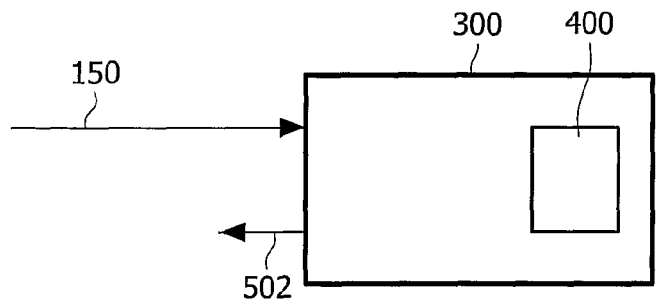
Figure 8:
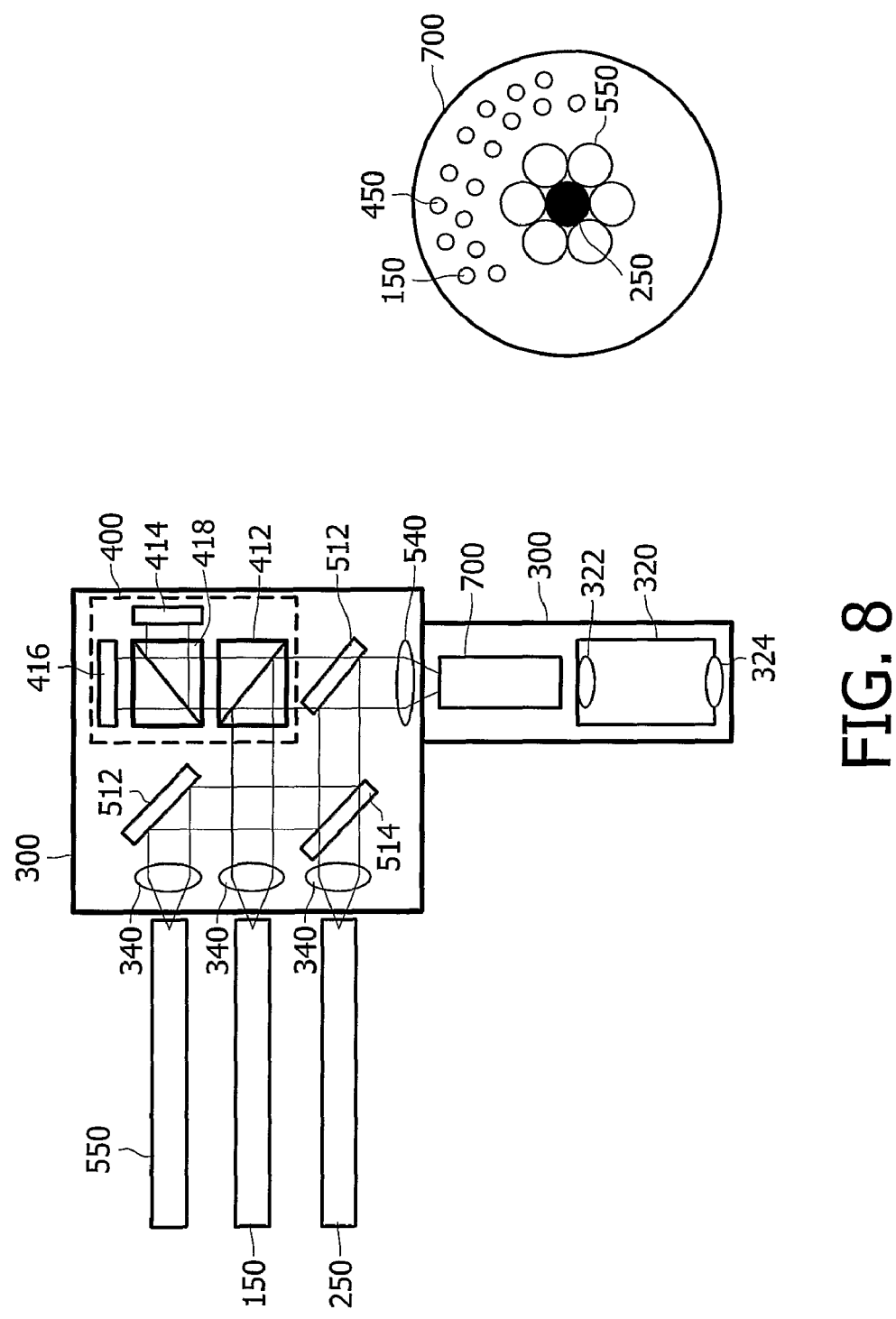
Figure 9:
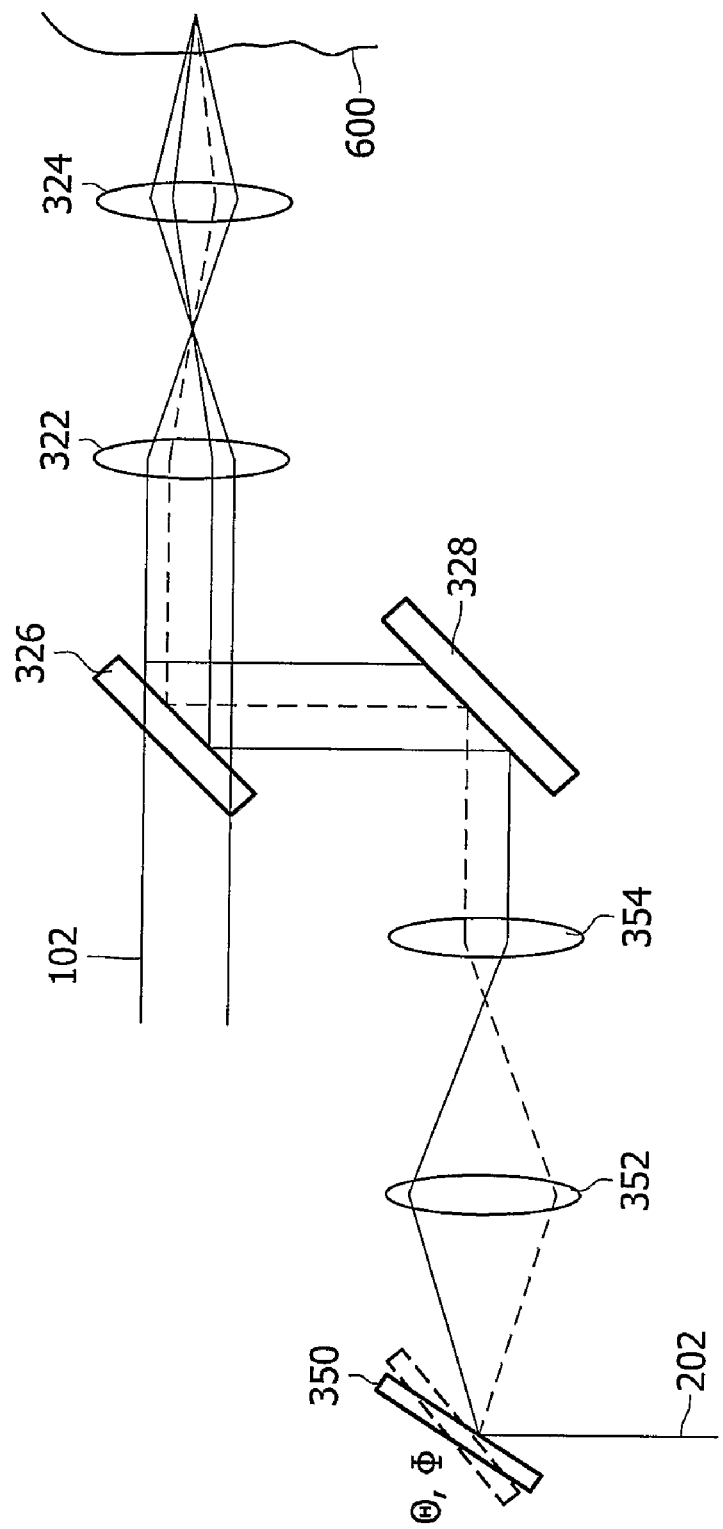
Figure 10:
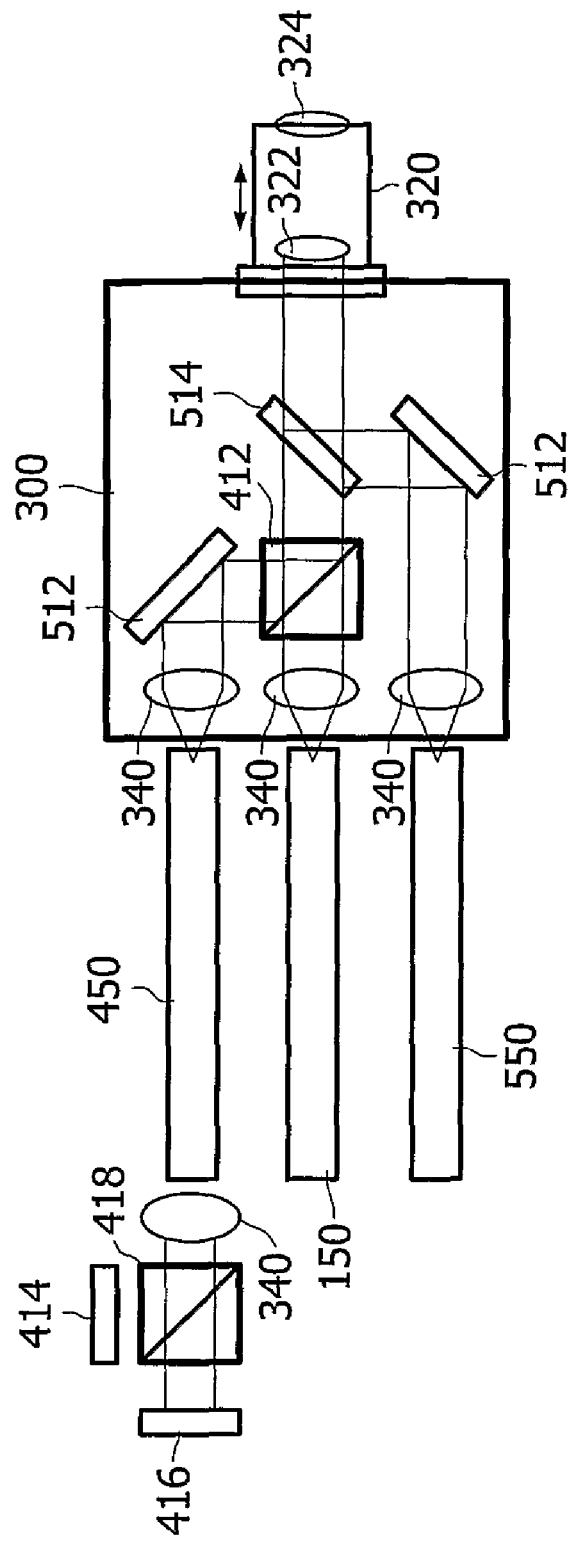

In the following, preferred embodiments of the invention will be described in greater detail by making reference to the drawings in which:

FIG. 1 shows a block diagram of the inventive spectroscopic system,

FIG. 2 shows a typical embodiment of the probe head incorporating a beam combination unit and a filter unit, FIG. 3 shows a block diagram of a beam combination unit, FIG. 4 shows a block diagram of a focusing unit incorporated into the objective of the probe head, FIG. 5 is illustrative of a block diagram of a probe head and an external beam combination unit, FIG. 6 illustrates a typical embodiment of a detection unit, FIG. 7 is illustrative of a block diagram of the probe head incorporating a detection unit for detecting and processing of monitoring return radiation, FIG. 8 is illustrative of a probe head incorporating a beam combination and a beam filtering unit as well as a focusing unit, FIG. 9 is illustrative of a shifting unit for arbitrarily shifting the focal position of the excitation beam, FIG. 10 shows a probe head incorporating a beam combination and beam separation unit as well as an external focusing unit.

FIG. 1 shows a block diagram of the inventive spectroscopic system comprising a probe head 300 and a base station 110. The base station 110 has a power supply 112, a monitoring beam source 100, an excitation beam source 200, a detection unit for the monitoring return radiation 400 and a detection unit 500 for the return radiation. The monitoring beam acts as an imaging beam for visually imaging the volume of interest. The corresponding monitoring return radiation 400 represents the elastically scattered portion of the monitoring beam that is not subject to a frequency shift due to an inelastic scattering process.

The return radiation in turn represents an inelastic scattered portion of the excitation beam. Hence, in the case of Raman and fluorescence spectroscopy the return radiation is frequency shifted with respect to the excitation beam and is therefore indicative of the molecular composition of a biological structure located within the volume of interest.

For example, the monitoring can be performed by making use of orthogonal polarized spectral imaging (OPS) and the spectroscopic analysis preferably exploits the Raman effect. In this case the excitation beam source 200 is implemented as a near-infrared light source for generating Raman scattering in a volume of interest 602 underneath the surface of a skin 600 of a patient. Correspondingly, the detection unit 500 is adapted to detect frequency shifted return radiation emerging from the volume of interest 602.

The base station 110 and the probe head 300 are connected by a flexible cable providing a plurality of optical fibers 150, 250, 450 and 550. Optical fiber 150 provides optical transmission of the monitoring beam from the monitoring beam source 100 to the probe head 300. Optical fiber 250 provides optical transmission of the excitation beam from the excitation beam source 200 to the probe head 300. Optical fiber 450 provides optical transmission of monitoring return radiation from the probe head 300 to the detection unit 400 for detecting monitoring return radiation. Optical fiber 550 provides optical transmission of return radiation, i.e. frequency shifted Raman scattered radiation from the probe head 300 to the detection unit 500 for detecting frequency shifted returning excitation radiation.

The cable 700 connecting the base station 110 and the probe head 300 further has an electrical conducting element 650 being adapted to provide the probe head 300 with power from the power supply 112 of the base station 110. The cable 700 is plugged to the probe head by means of the connector 302 of the probe head, even allowing a flexible coupling of the probe head to the base station, which is particularly advantageous for cleaning or maintenance of the probe head. Correspondingly, the base station 110 also provides a connector 114, for plugging the cable 700 to the base station 110.

In the embodiment illustrated in FIG. 1 each of the optical fibers 150, 250, 450 and 550 separately provide transmission of one particular optical signal between the base station 110 and the probe head 300. The probe head 300 further has an objective lens 324 for focusing the monitoring beam and the excitation beam into the volume of interest 602. Preferably, the objective lens 324 is part of an objective for directing the excitation beam into the volume of interest 602 and for collecting return radiation emerging from the volume of interest 602. Since the probe head 300 makes use of a single objective lens 324 for monitoring and spectrally analyzing the volume of interest 602, the corresponding optical beams and collected return radiation have to be combined and separated by the probe head 300, respectively.

FIG. 2 illustrates a possible embodiment of the probe head 300 incorporating a beam combination unit 310, a filter unit 510 as well as a focusing unit 330. The probe head 300 as shown in FIG. 2 is adapted to be connected to four separate optical fibers providing transmission of the monitoring beam 102 and the excitation beam 202 to the probe head 300 and providing transmission of the monitoring return radiation 402 and the return radiation 502 from the probe head 300 to the base station 110.

The filter unit 510 has a dichroic mirror 514 featuring a different reflectivity and transmission for the monitoring and the excitation beam, respectively. Furthermore, the filter unit 510 has a conventional mirror 512 for deflection of the return radiation and further has a coupling lens 504 being adapted to couple the return radiation 502 into the optical fiber 550. The focusing unit 330 has an objective 320 having at least one objective lens 324. Here, the objective 320 is adapted to be moved in a horizontal direction allowing for shifting the horizontal position of the focus of the excitation beam and the monitoring beam.

The beam combination unit 310 is adapted to axially combine the monitoring beam 102 and the excitation beam 202. Hence, the two combined beams emerge from the combination unit 310, propagate through the filter unit 510, i.e. get transmitted by the dichroic mirror 514, and enter the objective 320 of the focusing unit 330. The axially combined beams 102 and 202 are focused into the volume of interest 602 by means of the objective lens 324. Typically, at least a portion of the monitoring beam experience reflection in the volume of interest and can be detected by the objective lens 324 as monitoring return radiation. Similarly, a portion of the excitation beam can be detected as return radiation being frequency shifted with respect to the excitation beam, due to the Raman processes taking place in the volume of interest 602.

Both the monitoring return radiation and the frequency shifted return radiation are collected by the objective lens 324 of the objective 320 thereby propagating in an opposite direction with respect to the monitoring and the excitation beam. Since the monitoring return radiation is of the same frequency than the monitoring radiation, it is transmitted by the dichroic mirror 514 of the filter unit 510. It enters the beam combination unit 310, where it is coupled as monitoring return radiation 402 into the fiber 450. In contrast, the frequency shifted return radiation of the excitation beam experiences a high reflectivity at the dichroic mirror 514. Hence the frequency shifted return radiation gets reflected twice by the dichroic mirror 514 and the conventional mirror 512. Finally, the return radiation 502 is coupled to the fiber 550 by means of the coupling lens 504 of the filter unit 510.

FIG. 3 is illustrative of a beam combination unit 310 for axially combining the monitoring beam 102 and the excitation beam 202. The two beams 102, 202 are transmitted to the beam combination unit 310 by the optical fibers 150, 250, respectively. The beam combination unit 310 has two coupling lenses 340, a mirror 328 and a beam splitter 326. The optical fiber 150 provides the monitoring beam 102 that is coupled into the beam combination unit 310 via the upper coupling lens 340. The optical fiber 250 provides transmission of the excitation beam 202 that is coupled into the beam combination unit 310 via the lower coupling lens 340. The optical fibers 150, 250 and the coupling lenses 340 are arranged in such a way that the excitation beam 202 as well as the monitoring beam 102 substantially propagate parallel to each other and further exhibit a negligible beam divergence.

After being coupled into the beam combination unit 310, the monitoring beam 102 propagates through the beam splitter 326 without any remarkable deflection. The excitation beam 202 propagating substantially parallel to the monitoring beam 102 gets reflected by the mirror 328 and thereby experiencing a deflection of substantially 90 degrees. The reflected excitation beam 202 enters the beam splitter 326 substantially perpendicular to the propagation direction of the monitoring beam 102. At least a portion of the excitation beam 202 gets reflected by the beam splitter 326 at an angle of 90 degrees finally leading to a coaxial propagation of the monitoring beam 102 and the excitation beam 202.

FIG. 4 is illustrative of a typical embodiment of the focusing unit 330 having an objective 320 making use of a flexible arrangement of two objective lenses 322, 324. The horizontal position of the focal plane can be shifted horizontally in either direction indicated by the arrows. A shifting of the focal plane can either be realized by shifting the entire objective 320 with respect to the focusing unit 330 or by horizontally shifting one or both of the objective lenses 324, 322, respectively.

FIG. 5 is illustrative of a block diagram of the probe head 300 and an external beam combination unit 310. In this embodiment the beam combination unit 310 is implemented into the base station 110 of the spectroscopic system. Similar as illustrated above, the beam combination unit 310 is adapted to combine the excitation beam 202 and the monitoring beam 102. Consequently, the combined beams 102, 202 are transmitted to the probe head 300 by means of the optical fiber 150. In this case the probe head 300 only incorporates a focusing unit 330 and a filter unit 510 for separating the return radiation 502 from the monitoring return radiation 402. Consequently, the cable connecting the probe head 300 and the base station 110 only has to provide three optical fibers 150, 450 and 550. Transmission of optical signals from the base station 110 to the probe head 300 is in this case provided by a single optical fiber 150.

Furthermore, also the filter unit 510 can be implemented into the base station 110 allowing for an even more compact design of the probe head 300. In such a case, the functionality of the optical fibers 450, 550 can be incorporated into one single optical fiber providing transmission of both the return radiation and the monitoring return radiation from the probe head 300 to the base station 110.

FIG. 6 is illustrative of a block diagram of a detection unit 400 for detecting and processing the monitoring return radiation 402. The illustrated detection unit 400 is particularly applicable when the monitoring of the volume of interest 602 is performed by making use of OPS imaging techniques. The detection unit 400 has a coupling lens 440, a polarizing beam splitter 412, a beam splitter 418, a beam trap 420 and two detectors 414, 416. The monitoring return radiation 402 that is transmitted by means of the optical fiber 415 is coupled into the detection unit 400 by means of the coupling lens 440. The polarizing beam splitter 412 splits off the polarized and the de-polarized light of the monitoring return radiation 402. The polarized light is deflected by the polarizing beam splitter 412 and gets blocked by the beam trap 420. The de-polarized light of the monitoring return radiation 402 is transmitted by the polarizing beam splitter 412 and is substantially equally split by the subsequent beam splitter 418. Each of the two components of the de-polarized light emerging from the beam splitter 418 in perpendicular directions are detected by two separate detectors 414 and 416. The detectors 414, 416 are preferably implemented as charge coupled device (CCD) cameras. Detecting the split de-polarized beam by two separate CCD cameras is particularly advantageous for implementing an auto focus mechanism.

FIG. 7 is illustrative of a block diagram of the probe head 300 having a detection unit 400 as illustrated in FIG. 6. In this embodiment the monitoring return radiation 402 is already processed within the probe head 300 by making use of the detection unit 400. Therefore, the probe head 300 is connected to the base station 110 by a cable that contains only two optical fibers 150 and 550. The optical fiber 150 is adapted to transmit both the monitoring beam 102 as well as the excitation beam 202. Since the monitoring return radiation 402 is already processed within the probe head 300, the optical fiber 550 only serves to transmit the return radiation 502 from the probe head 300 to the base station 110. Moreover, the beam combination unit 310 is incorporated into the base station 110 and the filter unit 510 is implemented into the probe head 300.

Moreover, in this embodiment the probe head 300 further has a user interface that provides efficient usage of the handheld probe head. For this purpose the probe head features a button for initiating and/or stopping a zooming or tracking of a designated biological structure within the imaged volume of interest. In this way, the user gains an easy and intuitive control of tracing biological structures underneath the surface of the skin of the patient. Moreover, by means of such a user initiated tracking, the depth of focus of e.g. the excitation and/or monitoring beam may be arbitrarily modified by the user.

FIG. 8 illustrates an embodiment of the probe head 300 having a detection unit 400 and the components of a filter unit 510 as illustrated in FIG. 2. The cable connecting the probe head 300 with the base station 110 has three optical fibers 150, 250 and 550. Each of these fibers 150, 250, 550 serves to transmit only one of the optical signals. Since the detection unit 400 is incorporated into the probe head 300 there is no need for transmitting the monitoring return radiation 402 to the base station 110.

The detection unit 400 of the probe head 300 has the same functionality as the one illustrated by FIG. 6. It has two detectors 414, 416 and two beam splitters 418, 412, wherein the latter one is a polarizing beam splitter. In the illustrated embodiment of FIG. 8 the dichroic mirror 514, the beam splitter 512 as well as the polarizing beam splitter 412 serve as a beam combination unit similar as the one depicted in FIG. 3. Moreover, the two mirrors 512 and the dichroic mirror 514 serve as a filter unit in a similar way as the one illustrated by FIG. 2. The monitoring beam and the excitation beam that are provided by the two optical fibers 150 and 250, respectively are coupled into the probe head by making use of the coupling lenses 340. By means of the beam splitters 412 and 512 the two beams are axially aligned and directed towards the coupling lens 540.

The coupling lens 540 couples the two light beams into the cable 700 having a plurality of imaging fibers 150, 450, a single excitation fiber 250 and a plurality of fibers 550 being adapted to transmit frequency shifted return radiation from the objective 320 to the probe head 300. In this way, the cable 700 serves as a multi-fiber transmission system for providing the monitoring and excitation beam to the objective 320 and for providing the probe head 300 with return radiation, monitoring return radiation as well as excitation return radiation.

The cable 700 is preferably adapted as a flexible cable and allows for a flexible handling of the objective 320 of the probe head 300. The cable 700 maybe almost of any arbitrary length and therefore allows flexible handling of the objective of the probe head 300. The objective 320 has two objective lenses 322 and 324 being adapted to be vertically shifted in order to move the focal plane of the optical system.

Return radiation, either of monitoring or inelastically scattered excitation type, is collected by the objective lens 324 of the objective 320 and is transmitted by the various fibers 150, 250, 450, 550 of the flexible cable 700. Emerging from the flexible cable 700, the returning light gets collimated by the coupling lens 540 and split in half by the beam splitter 512. A part of the returning radiation is transmitted by the beam splitter 512 and enters the detection unit 400 and another part gets reflected at a 90 degree angle by the beam splitter 512. The reflected part containing both the monitoring as well as the spectroscopic signal then hits the dichroic mirror 514 which is especially designed for reflecting only the frequency shifted radiation that is due to a scattering process taking place inside the volume of interest 602. In this way, the dichroic mirror 514 allows to select only the frequency shifted parts of the return radiation providing the spectroscopic signal. This frequency shifted part of the return radiation getting reflected by the dichroic mirror 514 hits the mirror 512 deflecting the radiation towards the coupling lens 340, coupling the spectroscopic signal into the fiber 550. The fiber 550 then transmits the spectroscopic signal to the spectroscopic detection unit 500 of the base station 110.

In the embodiment illustrated in FIG. 8 the detection unit 400 as well as the components of the filter unit 512, 514 and 540 can either be implemented in the probe head 300 or alternatively in the base station 110. Making use of the flexible cable 700 having an arbitrary length allows to design the probe head 300 in such as way that it only contains the objective 320 with its two objective lenses 322 and 324.

FIG. 9 is illustrative of a scanning arrangement for shifting the excitation beam 202 with respect to the monitoring beam 102. FIG. 9 shows a combination of objective, beam combination unit and a scanning unit. The monitoring beam propagates through the beam splitter 326 and gets sufficiently focused inside the skin of the patient 600 by the arrangement of the two objective lenses 322 and 324. The beam splitter 326 serves to axially combine the monitoring beam 102 and the excitation beam 202.

Moreover, the excitation beam 202 propagates through a system of lenses 352, 354 and mirrors 350, 328. In particular, the mirror 350 is implemented as a scanning mirror device that can be tilted in both transverse directions $\Phi$ and $\theta$ with respect to the optical axis. Depending on the tilt angles $\Phi$ and $\theta$ of the scanning mirror 350 the excitation beam 202 follows different optical paths through the system of lenses 352, 354.

Preferably, the scanning mirror 350 is positioned in the focal plane of the lens system consisting of the two lenses 352 and 354. In this way it is guaranteed that the excitation beam 202 propagates parallel to the optical axis for any arbitrary tilt angle $\Phi$, $\theta$ of the scanning mirror 350. Hence the excitation beam 202 only experiences a lateral translation by the system of scanning mirror 350, and the two lenses 352, 354.

Reflection at the mirror 328 and the beam splitter 326 provide a parallel shifting of the excitation beam 202 with respect to the monitoring beam 102. Due to the transverse shifting of the excitation beam 202 the focal position of the excitation beam slightly shifts with respect to the focal position of the monitoring beam 102 when the two beams 102, 202 propagate through the system of objective lenses 322 and 324.

In this way, not only the position of the focal plane can be shifted with respect to the skin 600 of the patient but also the position of the focal spot of the excitation beam 202 can be arbitrarily shifted with respect to the focal position of the monitoring beam 102.

FIG. 10 is illustrative of another embodiment of the probe head 300 incorporating various components of the detection unit 400 and the filter unit 510. Here, the probe head has three coupling lenses 340, a polarizing beam splitter 412, a dichroic mirror 514, a mirror 512 and an objective 320 with two objective lenses 322, 324. In this embodiment, parts of the detection unit 400 that has been separately illustrated by FIG. 6 are implemented as external device consisting of two detectors 414, 416 a coupling lens 340 and a beam splitter 418.

The polarizing beam splitter 412 typically belonging to the detection unit 400 is in this embodiment implemented separately into the probe head 300. The probe head 300 is coupled to the beam splitter 418 by means of the optical fiber 450 being adapted to transmit monitoring return radiation 402 from the probe head 300 to the two separate detectors 414 and 416. The optical fiber 150 is adapted to transmit the monitoring beam 102 and the excitation beam 202 to the probe head 300. The two beams 102, 202 emerging from two different light sources are already combined by the base station, propagate straight through the beam splitter 412 and the dichroic element 514 into the objective 320. By means of the objective lens 324 the two beams are finally focused into the volume of interest from where parts of the emitted radiation return to the objective 320.

By means of the dichroic mirror 514 the frequency shifted return radiation that stems e.g. from various Raman processes gets reflected to the mirror 512 directing the return radiation to the coupling lens 340 coupling the frequency shifted light into the optical fiber 550 transmitting the spectroscopic signal to the base station 110.

Return radiation that does not get reflected by the dichroic element 514 propagates to the beam splifter 412, where a part of the return radiation is reflected to the mirror 512 directing the radiation to the coupling lens 340 for coupling the return light into the fiber 450. This part of the return light is then transmitted to the beam splitter 418 splitting the optical signal in order to be separately detected by the detectors 414 and 416. Preferably the optical fibers 150, 450, 550 are all incorporated into a single flexible cable connecting the probe head 300 with the base station 110.

LIST OF REFERENCE NUMERALS 100 monitoring beam source
102 monitoring beam
110 base station
112 power supply
150 fiber
200 excitation beam source
202 excitation beam
250 fiber
300 probe head
302 connector
310 beam combination unit
320 objective
322 objective lens
324 objective lens
326 beam splitter
328 mirror
330 focusing unit
340 coupling lens
350 scanning mirror
352 lens
354 lens
400 detection unit
402 monitoring return radiation
412 polarizing beam splitter
414 detector
416 detector
418 beam splitter
420 beam trap
440 coupling lens
450 fiber
500 detection unit
502 return radiation
504 coupling lens
510 filter unit
512 beam splitter
514 dichroic mirror
540 coupling lens
550 fiber
600 skin
602 volume of interest
650 electrical conductor
700 cable

The invention claimed is:

1. A spectroscopic system for determining a property of a fluid flowing through a volume of interest underneath the surface of the skin of a patient, the spectroscopic system comprising:
a probe head having an objective for directing an excitation beam into the volume of interest and for collecting return radiation from the volume of interest,
a base station having a spectroscopic analysis unit, an excitation beam source, a monitoring beam source, and a power supply,
a cable connecting the probe head and the base station for transmission of the return radiation from the probe head to the base station and for providing the probe head with power from the power supply of the base station, wherein
the cable comprises an optical fiber adapted to transmit a monitoring beam to the probe head.

2. The spectroscopic system according to claim 1, wherein the probe head further comprising a beam combination unit for axially combining the excitation beam and the monitoring beam.

3. The spectroscopic system according to claim 1, wherein the probe head further comprising a filter unit for spatially separating the return radiation and the monitoring return radiation.

4. The spectroscopic system according to claim 1, wherein the probe head further comprising a focusing unit being adapted to move a focal volume of the excitation beam into the volume of interest.

5. The spectroscopic system according to claim 1, wherein a probe head further comprising an optical imaging unit for analyzing the monitoring return radiation.

6. The spectroscopic system according to claim 1, wherein the base station further comprising a beam combination unit for axially combining the excitation beam and the monitoring beam.

7. The spectroscopic system according to claim 1, wherein the base station further comprising a filter unit for spatially separating the return radiation and the monitoring return radiation.

8. The spectroscopic system according to claim 1, wherein the base station further comprising a focusing unit being adapted to move a focal volume of the excitation beam into the volume of interest.

9. The spectroscopic system according to claim 1, wherein the base station further comprising an optical imaging unit for analyzing the monitoring return radiation.

10. The spectroscopic system according to claim 1, wherein the optical imaging unit being adapted to select the volume of interest and being further adapted to control a focusing unit moving a focal volume of the excitation beam into the volume of interest.

11. A probe head for a spectroscopic system for determining a property of a fluid flowing through a volume of interest underneath the surface of the skin of a patient, the spectroscopic system having a base station with a spectroscopic analysis unit and a power supply, the probe head comprising:
an objective for directing an excitation beam into the volume of interest and for collecting return radiation from the volume of interest, a connector for connecting the probe head to a cable being coupled to the base station, the cable being adapted to provide transmission of the return radiation from the probe head to the base station, to provide a monitoring beam from the base station to the probe head, and to provide the probe head with power from the power supply of the base station, and a beam combination unit configured to combine the monitoring beam with the excitation beam.

12. A base station for a spectroscopic system for determining a property of a fluid flowing through a volume of interest underneath the surface of the skin of a patient, the spectroscopic system having a probe head having an objective for directing an excitation beam into the volume of interest and for collecting return radiation from the volume of interest, the base station comprising:

a spectroscopic analysis unit and a power supply, a connector for connecting the base station to a cable being coupled to the probe head, the cable being adapted to provide transmission of the return radiation from the probe head to the base station and to provide the probe head with power from the power supply of the base station, and an excitation beam source and a monitoring beam source configured to provide the excitation beam and a monitoring beam to the volume of interest through the connector.

* * * * *